United States Patent [19]

Peterson et al.

[11] Patent Number: 5,563,036
[45] Date of Patent: Oct. 8, 1996

[54] TRANSCRIPTION FACTOR-DNA BINDING ASSAY

[75] Inventors: Michael G. Peterson; Vijay R. Baichwal; Berta Strulovici, all of So. San Francisco, Calif.

[73] Assignee: Tularik, Inc., South San Francisco, Calif.

[21] Appl. No.: 235,503

[22] Filed: Apr. 29, 1994

[51] Int. Cl.$^6$ .................................................... C12Q 1/68
[52] U.S. Cl. ............................................................ 435/6
[58] Field of Search ...................................... 435/6

[56] References Cited

U.S. PATENT DOCUMENTS

| | | | |
|---|---|---|---|
| 4,789,628 | 12/1988 | Nayak | 435/7.94 |
| 4,816,730 | 3/1989 | Wilhelm, Jr. et al. | 318/568.22 |
| 5,200,051 | 4/1993 | Cozzette et al. | 204/403 |
| 5,453,362 | 9/1995 | Lamarco et al. | 435/69.1 |

FOREIGN PATENT DOCUMENTS

46637/89  12/1989  WIPO .

OTHER PUBLICATIONS

Kemp et al., "Simplified Colorimetric Analysis of Polymerase Chain Reactions: Detection of HIV Sequences in AIDS Patients", *Gene* 94:223–228 (1990).

Kemp et al., "Colorimetric Detection of Specific DNA Segments Amplified by Polymerase Chain Reactions", *Proc. Natl. Acad. Sci. USA* 86:2423–2427 (1989).

Jost et al., Nucleic Acids Research, vol. 19(10): p. 2788, (1991).

Gambari et al., Proceedings of the American Association for Cancer Research, vol. 32: p. 333, (1991).

Peterson et al., Trends in Biotechnology, vol. 11(1): pp. 11–18, (Jan., 1993).

*Primary Examiner*—George C. Elliott
*Assistant Examiner*—Terry A. McKelvey
*Attorney, Agent, or Firm*—Flehr, Hohbach, Test, Albritton & Herbert

[57] ABSTRACT

Pharmacological agents useful in the diagnosis or treatment of disease associated with the expression of a gene are identified in high throughput drug screening assays. The methods involve combining a labeled transcription factor, a nucleic acid coupled to a ligand, a candidate pharmacological agent and a receptor immobilized on a solid substrate, such as a microtiter plate, filter, or bead. The nucleic acid has at least that portion of a nucleotide sequence naturally involved in the regulation of the transcription of the gene which is necessary for sequence-specific interaction with the transcription factor. The resultant combination is incubated under conditions whereby the receptor is bound to the ligand and, but for the presence of said candidate pharmacological agent, the transcription factor is sequence-specifically bound to the nucleic acid. Unbound transcription factor is then removed or washed from the solid substrate and labelled, sequence-specifically bound transcription factor is detected. Incubates which include candidate agents which alter transcription factor binding deviate from control incubates in terms of label signal—typically, binding is disrupted and the signal is diminished. In a preferred embodiment, the entire process is performed by a computer-controllable electromechanical robot with an axial rotatable arm.

14 Claims, 1 Drawing Sheet

TRANSCRIPTION FACTOR-DNA BINDING ASSAY

INTRODUCTION

1. Field of the Invention

The field of this invention is assays for screening for drugs which interfere with sequence-specific protein-DNA binding.

2. Background

Half the U.S. population is infected with Herpes Simplex Virus (HSV) type 1. A quarter of the U.S. population is infected with HSV type 2. Over a million Americans are infected with HIV. About 1% of all newborns in the U.S. have congenital cytomegalovirus infection. The numbers are staggering, yet effective therapeutics are unavailable for these and most other viral infections. A similar deficiency is found in treatments of heart disease, cancer and many other of significant threats to modern human health.

Gene-specific transcription factors provide a promising class of targets for novel therapeutics directed to these and other human diseases for the following reasons. One, transcription factors offer substantial diversity. Over 300 gene-specific transcription factors have been described, and the human genome may encode as many as 3000. Hence, they provide as plentiful a target source as cell-surface receptors. Two, transcription factors offer substantial specificity. Each and every factor offers unique molecular surfaces to target. Three, transcription factors are known to be involved in human disease. For example, many tumors are associated with the activation of a specific oncogene. A third of known proto-oncogenes and three fourths of all anti-oncogenes are transcription factors.

A number of extremely effective presently marketed drugs act, at least indirectly, by modulating gene transcription. For instance, in many cases of heart disease, the LDL receptor is pathogenically down-regulated at the level of transcription by intracellular sterol levels. The drug compactin, an inhibitor of HMC CoA reductase, functions by up-regulating transcription of the LDL receptor gene which leads to clearance of cholesterol from the blood stream.

Identifying and developing new pharmaceuticals is a multibillion dollar industry in the U.S. alone. Urgently needed are efficient methods of identifying pharmacological agents or drugs which are active at the level of gene transcription. If amenable to automated, cost-effective, high throughput drug screening, such methods would have immediate application in a broad range of domestic and international pharmaceutical and biotechnology drug development programs.

Relevant Literature

Kemp, D. J., Foote, S. J., Peterson, M. G., Samaras, N., and Smith, D. et at. (1989) Amplified DNA Assay. PCT International Application Number 46637/89 (Filed 8 Dec. 1989).

Kemp, D. J., et at. (1990) Simplified colorimetric analysis of polymerase chain reactions: detection of HIV sequences in AIDS patients. Gene 94, 223–228.

Kemp, D. J. et at. (1989) Colorimetric detection of specific DNA segments amplified by polymerase chain reactions. PNAS USA 86, 2423–2427.

SUMMARY OF THE INVENTION

The invention provides methods for identifying pharmacological agents useful in the diagnosis or treatment of disease associated with the expression of a gene.

In general, the methods involve combining a labeled protein, a nucleic acid, a candidate pharmacological agent and a receptor immobilized on a solid substrate, such as a microtiter plate. The labelled protein includes at least a portion of a natural transcription factor involved in the regulation of the gene's expression. The nucleic acid has at least that portion of a nucleotide sequence naturally involved in the regulation of the transcription of the gene which is necessary for sequence-specific interaction, direct or indirect, with the transcription factor. The nucleic acid is conjugated to a ligand capable of specificity binding the immobilized receptor. The resultant mixture is incubated under conditions whereby the receptor is bound to the ligand and, but for the presence of said candidate pharmacological agent, the transcription factor is sequence-specifically bound to the nucleic acid. Unbound transcription factor is then removed or washed from the solid substrate and labelled, sequence-specifically bound transcription factor is detected. Binding reactions, "incubates", which include candidate agents which alter transcription factor binding deviate from control incubates in terms of label retained on the substrate—typically, binding is disrupted and the signal is diminished. In this way, pharmacological agents which modulate transcription factor-gene interactions are identified.

A wide variety of alternative embodiments of the general method are disclosed. These include a variety of labels, ligands, receptors, genes, transcription factors, auxiliary factors, etc. In a preferred embodiment, the transcription factor is vital or eukaryotic, the label is a radioactive atom, the receptor is avidin and the ligand is biotin. Much of the method is amenable to performance by electromechanical robot. In a preferred embodiment, the method is performed by a computer-controllable electromechanical robot with an axial rotatable arm. In addition, the invention provides kits for drug screening based on the disclosed nucleic acid binding methods.

DETAILED DESCRIPTION OF THE INVENTION

Figure 1:
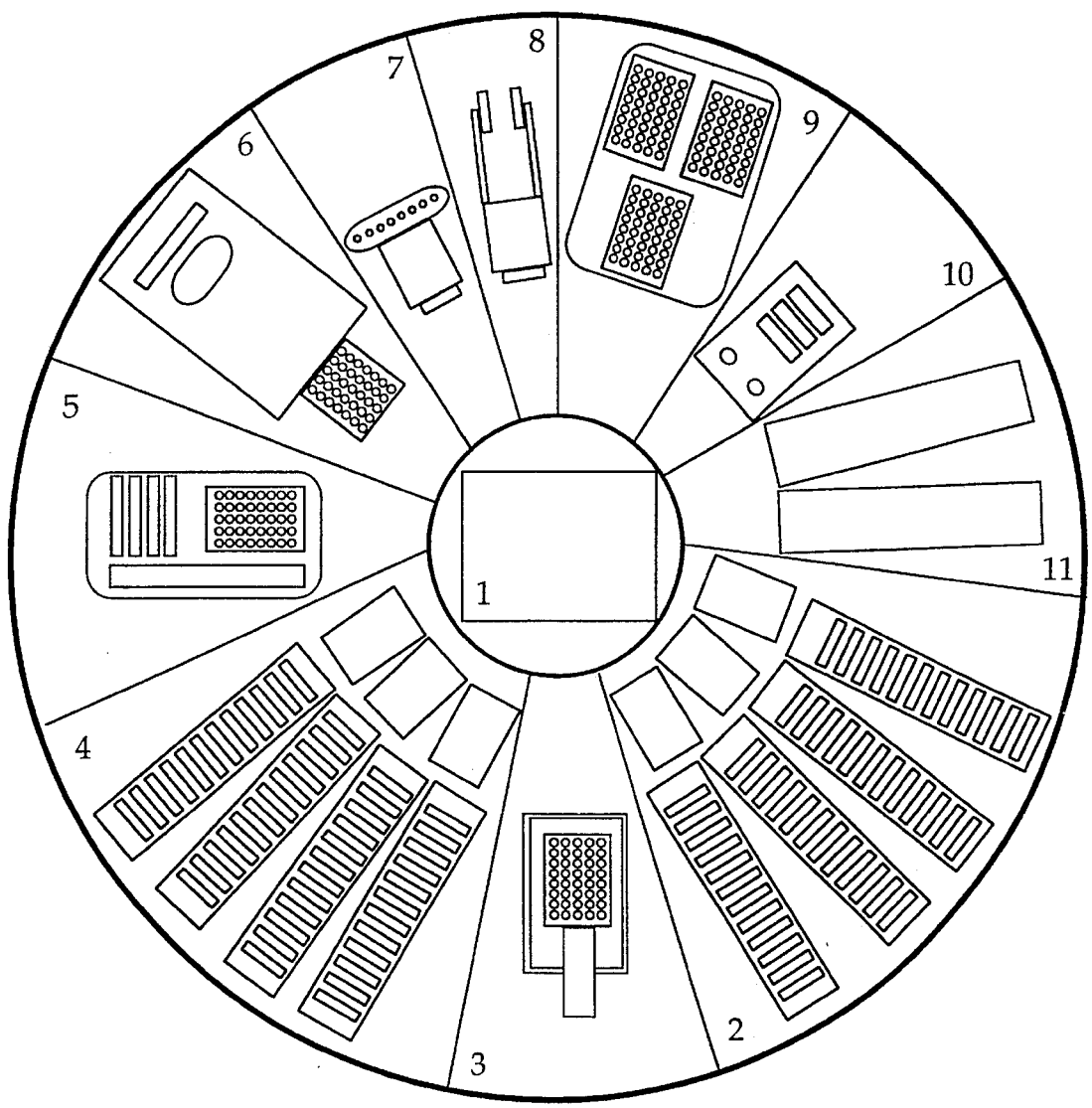
FIG. 1: Schematic of robotic station design.

The invention provides efficient methods of identifying pharmacological agents or drugs which are active at the level of gene transcription. The methods are amenable to automated, cost-effective high throughput drug screening and have immediate application in a broad range of domestic and international pharmaceutical and biotechnology drug development programs.

Target diseases are limited only in that disease or disease progression be subject to inhibition by alteration of the specific interaction of a transcription factor and a gene or gene regulatory region. As such, target diseases include viral, bacterial and fungal infections, metabolic disease, genetic disease, cell growth and regulatory disfunction, such as neoplasia, inflammation, hypersensitivity, etc. The target diseases may be afflictions of plants, especially agricultural crops, or animals, especially livestock, house animals and humans.

Transcription factors are capable of sequence-specific interaction with a portion of a gene or gene regulatory region. The interaction may be direct sequence-specific binding where the transcription factor directly contacts the nucleic acid or indirect sequence-specific binding mediated or facilitated by other auxiliary proteins where the transcription factor is tethered to the nucleic acid by a direct nucleic acid binding protein. In addition, some transcription factor demonstrate induced or synergistic binding. A broad range of transcription factor-nucleic acid complexes provide useful targets. The gene and/or transcription factor may be derived from a host or from an infectious or parasitic organism. As examples, a host may be immunomodulated (e.g. by controlling inflammation or hypersensitivity) by modulating the DNA binding of a transcription factor involved in immune cell activation; or viral, bacterial, or other microbial disease progression may be inhibited by disrupting the DNA binding of a host, viral or other microbial transcription factor involved in viral or other microbial gene transcription.

Applicable host and viral or microbial transcription factors and corresponding oligonucleotide targets are found in sources such as the regularly updated Transcription Factor Database of the National Center for Biotechnology Information at the National Library for Medicine and Faisst and Meyer (1991) Nucleic Acids Research 20, 3-26. Preferred pain are listed in Table 1 below.

| Factor[1] | Binding Sequence[3] |
|---|---|
| AAF | TTTCATATTACTCT (SEQ ID NO:1) |
| AhR | TGCGTGAGAAGA (SEQ ID NO:2) |
| Ap1 | TGASTMA |
| AP2 | CCCMCNSSS |
| AP3 | TGTGGWWW |
| AP4 | YCAGCTGYGG (SEQ ID NO:3) |
| AR | AGAACANNNTGTTCT (SEQ ID NO:4) |
| ARP-1 | TGANCCCTTGACCCCT (SEQ ID NO:5) |
| ATF | TGACGYMR |
| BGP1 | GGGGGGGGGGGGGGGG (SEQ ID NO:6) |
| BSAP | GACGCANYGRWNNNMG (SEQ ID NO:7) |
| CBF | ACACCCAAATATGGCGAC (SEQ ID NO:8) |
| C/EBP | GTGGWWWG |
| CF1 | ANATGG |
| COUP | GTGTCAAAGGTCA (SEQ ID NO:9) |
| CP1 | YNNNNNNRRCCAATCANYK (SEQ ID NO:10) |
| CP2 | YAGYNNNRRCCAATCNNNR (SEQ ID NO:11) |
| CTCF | CCCTC |
| DBP | TGATTTTGT |
| E2A | RCAGNTG |
| E2B | TGCAAYAY |
| E2F | TTTTSSCGS |
| E4F | TGACGTAAC |
| EGR-1 | CGCCCSCGC |
| EGR-2 | CCGCCCCGC (SEQ ID NO:12) |
| ER | AGGTCANNNTGACCT (SEQ ID NO:13) |
| v-ErbA | GTGTCAAAGGTCA (SEQ ID NO:14) |
| ETF | CAGCCCCCGCGCAGC (SEQ ID NO:15) |
| Ets-1 | SMGGAWGY |
| F-ACT1 | TGGCGA |
| GATA-1 | WGATAR |
| GATA-2 | WGATAR |
| GATA-3 | WGATAR |
| GCF | SCGSSSC |
| GHF-1 | WTATYCAT |
| GHF-5 | WTATYCAT |
| GHF-7 | WTATYCAT |
| GR | AGAACANNNTGTTCT (SEQ ID NO:16) |

| Factor[1] | Binding Sequence[3] |
|---|---|
| H1TF2 | GCACCAATCACAGCGCGC (SEQ ID NO:17) |
| H2RIIBP | TCAGGTCACAGTGACCTGA (SEQ ID NO:18) |
| H2TF1 | TGGGGATTCCCCA (SEQ ID NO:19) |
| H-APF-1 | CTGGRAA |
| HNF-1 | GTTAATNATTAAC (SEQ ID NO:20) |
| vHNF-1 | GTTAATNATTAAC (SEQ ID NO:20) |
| HNF-3A | TATTGAYTTWG (SEQ ID NO:21) |
| HNF-3B | TATTGAYTTWG (SEQ ID NO:21) |
| HNF-3C | TATTGAYTTWG (SEQ ID NO:21) |
| HNF-4 | KGCWARGKYCAY (SEQ ID NO:22) |
| HSF | NGAANNGAANNGAAN (SEQ ID NO:23) |
| IAF | GCCATCTGCT (SEQ ID NO:24) |
| IREBF-1 | CGGGAAATGGAAACTG (SEQ ID NO:25) |
| IRBP | AGTGCACT |
| ISGF1 | CTTTCAGTTT (SEQ ID NO:26) |
| ISGF2 | CTTTCTCTTT (SEQ ID NO:27) |
| ISGF3 | GCTTCAGTTT (SEQ ID NO:28) |
| KBF-1 | TGGGGATTCCCCA (SEQ ID NO:29) |
| Ker1 | GCCTGCAGGC (SEQ ID NO:30) |
| LFB3 | GTTAATNATTAAC (SEQ ID NO:31) |
| LIT-1 | GCGCCCTTTGGACCT (SEQ ID NO:32) |
| LyF-1 | PPTGGGAGR |
| MBF-1 | YTAAAAATAAYYY (SEQ ID NO:33) |
| MBF-I | TGCRCRC |
| MBP-1 | TGGGGATTCCCCA (SEQ ID NO:34) |
| MCBF | CATTCCT |
| MEF-2 | YTAWAAATAR (SEQ ID NO:35) |
| MEP-1 | TGCRCNC |
| MR | AGAACANNNNTGTTCT (SEQ ID NO:36) |
| Myb | YAACKG |
| Myc | CACGTG |
| | TCTCTTA |
| MyoD | CAACTGAC |
| NF1 | YGGMNNNNNGCCAA (SEQ ID NO:37) |
| NF-AT | GGAGGAAAAACTGTTTCAT (SEQ ID NO:38) |
| NF-E2 | TGACTCAG |
| NF-D | GATGGCGG |
| NF-GMa | GRGRGTTKCAY (SEQ ID NO:39) |
| NF-GMb | TCAGRTA |
| NF-IL6 | TKNNGNAAK |
| NFxB | GGGAMTNYCC (SEQ ID NO:40) |
| NF-W1 | GTTGCATC |
| NF-W2 | GTTGCATC |
| NGF1-B | AGGTCATGACCT (SEQ ID NO:41) |
| Oct-1 | ATGCAAAT |
| Oct-2 | ATGCAAAT |
| Oct-4 | ATGCWAAT |
| Oct-6 | ATGCAAAT |
| Pax-1 | CACCGTTCCGCTCTAGATATCTC (SEQ ID NO:42) |
| PCF | AGAAAGGGAAAGGA (SEQ ID NO:43) |
| PEA3 | AGGAAR |
| PPAR | AGGTCA |
| PR | AGAACANNNTGTTCT (SEQ ID NO:44) |
| PRDI-BF1 | AAGTGAAAGT (SEQ ID NO:45) |
| PTF1 | ATGGGANCTCAGCTGTGC (SEQ ID NO:46) |
| Pu.I | AGAGGAACT |
| PuF | GGGTGGG |
| RAR | AGGTCATGACCT (SEQ ID NO:47) |
| RFX | CCCCTAGCAACAGATG (SEQ ID NO:48) |
| RVF | AAGATAAACC (SEQ ID NO:49) |
| SIF | CCCGTM |
| Sp1 | KRGGCTRRK |
| SRF | GGATGTCCATATTAGGACATCT (SEQ ID NO:50) |
| TBP | TATAAA |
| TCF-1 | MAMAG |
| TCF-2α | SAGGAAGY |
| TEF-1 | AAGYATGCA |
| TEF-2 | GGGTGTGG |

| Factor[1] | Binding Sequence[3] |
|---|---|
| TGT3 | AAGTGTTTGC (SEQ ID NO:51) |
| TIN-1 | AGGAAGTTCC (SEQ ID NO:52) |
| WT-ZFP | CGCCCCCGC |
| XF1/2 | TCTTCTCACGCAACT (SEQ ID NO:53) |
| XPF-1 | CACCTGNNNNTTTCCC (SEQ ID NO:54) |
| YB-1 | ATTTTTCTGATTGGCCAAAG (SEQ ID NO:55) |
| Epstein-Barr Virus EBNA (B958 strain) | GGT TAG CAT ATG CTA ACC A (SEQ ID NO:56) |
| Epstein-Barr Virus BZLF (B958 strain) | T TAG CAA TG |
| Human CBF-1 | CGTGGGAA (EpsteinBarr Virus cis-element) |
| Human Papilloma Virus E2 (strain 6) | A CCG AAA ACG GTG T (SEQ ID NO:57) |
| Herpes Simplex Virus Type 1 VP16 | ATG CTA ATG ATA (SEQ ID NO:58) |
| HIV TAT | GGG TCT CTC TGG TTA GAC CAG ATC TGA GCC TGG GAG CTC TCT GGC TAA CTA GGG AAC CCA (SEQ ID NO:59) (TAR RNA SEQUENCE) |

The disclosed methods and kits involve reconstituting, in vitro, sequence-specific transcription factor-nucleic acid interactions, and challenging the reconstitution with candidate therapeutics. Preferred applications of the method include gene transcriptional regulation where at least one transcription factor and corresponding gene or gene regulatory region have been molecularly cloned. The methods involve forming a mixture of a labelled protein comprising at least a potion of a transcription factor, a nucleic acid conjugated to a ligand, a candidate pharmacological agent and a receptor immobilized on a solid substrate.

The labelled protein comprises at least a portion of a transcription factor and a label, the potion being sufficient to permit sequence-specific binding, direct or indirect, of the labelled protein to the nucleic acid conjugate. The portion is usually at least about 20, more usually at least about 40, most usually at least about 80 amino acids in length and includes residues sufficient to provide the protein with sequence-specificity similar to that of the native transcription factor. Frequently, the labelled protein will include the entire transcription factor. The labelled protein is typically capable of binding the nucleic acid conjugate with an equilibrium constant at least about $10^4 M^{-1}$, preferably at least about $10^6 M^{-1}$, more preferably at least about $10^8 M^{-1}$ and not less than six, preferably not less than four, more preferably not less than two orders of magnitude less than the binding equilibrium constant of the native transcription factor under similar conditions.

Preferred transcription factor portions capable of imparting the requisite binding specificity and affinity are readily identified by those skilled in the art. A wide variety of molecular and biochemical methods are available for generating preferred portions, see e.g. Molecular Cloning, A Laboratory Manual (2nd Ed., Sambrook, Fritsch and Maniatis, Cold Spring Harbor), Current Protocols in Molecular Biology (Eds. Aufubel, Brent, Kingston, More, Feidman, Smith and Stuhl, Greene Publ. Assoc., Wiley-Interscience, NY, N.Y., 1992) or that are otherwise known in the art. For example, deletion routants are screened for sequence-specific binding directly using a label or through gel shift analysis.

The labelled protein also comprises a label which is used to detect labelled protein-nucleic acid complexes. A wide variety of labels may be employed—essentially any label that provides for detection of the labelled protein when complexed to the nucleic acid conjugate. The label may provide for direct detection as radioactivity, luminescence, optical or electron density, etc. or indirect detection such as an epitope tag, an enzyme, etc. The label may be appended to the protein e.g. a phosphate group comprising a radioactive isotope of phosphorous, or incorporated into the protein structure, e.g. a methionine residue comprising a radioactive isotope of sulfur.

The protein may also comprise additional components depending upon the assay reagents and conditions. For example, it may be desirable that the protein be a fusion product of the transcription factor portion and another polypeptide, e.g. a polypeptide that is capable of providing or enhancing sequence-specific nucleic acid binding or stability under assay conditions.

The nucleic acid conjugate comprises a nucleic acid coupled to a ligand. The nucleic acid is usually linear and double-stranded DNA or RNA, particularly in the case of retroviral transcription factor binding sites, though circular plasmids or other nucleic acids or structural analogs may be substituted so long as transcription factor sequence-specific binding is retained. In some applications, supercoiled DNA provides optimal sequence-specific binding and is preferred. The nucleic acid may be of any length amenable to the assay conditions and requirements. Typically the nucleic acid is between 8 bp and 5 kb, preferably between about 12 bp and 1 kb, more preferably between about 18 bp and 250 bp, most preferably between about 27 and 50 bp.

The nucleic acid has a sequence at least a portion of which is common to the gene or gene regulatory region to which the native transcription factor normally binds. The portion may be continuous or segmented and shares sufficient sequence and sequence similarity with the gene or gene regulatory region to provide sequence-specific binding of the labelled protein. Typically, this binding site portion of the nucleic acid constitutes at least about 4, preferably at least about 6, more preferably at least about 8 nucleotides. Additional nucleotides may used to provide structure which enhances or decreased binding or stability, etc. For example, combinatorial DNA binding can be effected by including two or more DNA binding sites for different or the same transcription factor on the oligonucleotide. This allows for the study of cooperative or synergistic DNA binding of two or more factors, eg. HPV E1 and E2 bind cooperatively to DNA by virtue of their protein-protein interaction. In addition, the nucleic acid can comprise a cassette into which transcription factor binding sites are conveniently spliced for use in the subject assays. An exemplary cassette showing how new DNA binding sites can be exchanged in a simple fashion within a common 30-mer sequence appears in Table 2 below.

TABLE 2

| EBV EBNA-1 site | GGA TCT GGT TAG CAT ATG CTA ACC AGG ATC (SEQ ID NO:60) |
|---|---|
| HPV E2 substituted | GGA TCT GGT ACC GAA AAC GGT ACC AGG ATC (SEQ ID NO:61) |

TABLE 2-continued

| EBV BZLF-1 substituted | GGA TCT GGT TAG TTA GCA ATG ACC AGG ATC (SEQ ID NO:62) |
| NF-kB and homologs | GGA TCT GGT TAG GGG ATT TCC ACC AGG ATC (SEQ ID NO:63) |
| HSV VP16 cis-element | GGA TCT GGT TAT GCT AAT GAT ATC AGG ATC (SEQ ID NO:64) |

The ligand of the nucleic acid conjugate is capable of specifically binding the immobilized receptor. The ligand-receptor binding is specific enough to provide a maximized and at least measurable signal to noise ratio (receptor mediated vs. non-specific retention of the label on the substrate). The nucleic acid conjugate is typically capable of binding the receptor with an affinity of at least about $10^5 M^{-1}$, preferably at least about $10^6 M^{-1}$, more preferably at least about $10^8 M^{-1}$. In a preferred embodiment, a plurality of ligands are capable of binding each receptor. Exemplary ligand-receptor pairs include biotin and avidin, antigen and antibody, sugar and lectin, ion and chelator, etc.

The receptor is immobilized on a solid substrate which may be any solid from which the unbound labelled protein may be conveniently separated. The solid substrate may be made of a wide variety of materials and in a wide variety of shapes, e.g. microfiter plate, microbead, dipstick, resin particle, etc. The substrate is chosen to maximize signal to noise ratios, primarily to minimize background binding, for ease of washing and cost. For example, beads with iron cores may be readily isolated (washed) using magnets.

The mixture aim comprises a candidate pharmacological agent. Candidate agents encompass numerous chemical classes, though typically they are organic compounds; preferably small organic compounds. Small organic compounds have a molecular weight of more than 50 yet less than about 2,500, preferably less than about 1000, more preferably, less than about 500. Candidate agents comprise functional chemical groups necessary for structural interactions with proteins and/or DNA, and typically include at least an amine, carbonyl, hydroxyl or carboxyl group, preferably at least two of said functional chemical groups, more preferably at least three. The candidate agents often comprise cyclical carbon or heterocyclic structures and/or aromatic or polyaromatic structures substituted with one or more of the forementioned functional groups. Candidate agents are also found among biomolecules including peptides, saccharides, fatty acids, steroids, purines, pyrimidines, derivatives, structural analogs or combinations thereof, and the like.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural and synthetically produced libraries and compounds are readily modified through conventional chemical, physical, and biochemical means. In addition, known pharmacological agents may be subject to directed or random chemical modifications, such as acylation, alkylation, esterification, amidification, etc., to produce structural analogs.

In addition to the labelled protein, nucleic acid conjugate, candidate agent and immobilized receptor, the mixture usually includes additional reagents, such as salts, buffers, etc. to facilitate optimal receptor-ligand and protein-nucleic acid binding. Auxiliary proteins or portions thereof may also be included to mediate, facilitate or otherwise enhance sequence-specific protein-nucleic acid binding. For example, sequence-specific binding of a number of viral transcription factors is enhanced when complexed with one or more cellular proteins, e.g. Octl and HCF in the case of HSV's VP16. Other exemplary auxiliary proteins include CBF1, for EBNA-2 binding, ATF-2 or AP-1 for Adenovirus E1A binding, etc.

A variety of other reagents may also be included in the mixture. These include reagents like detergents which may be used to reduce non-specific or background protein-substrate, nucleic acid-substrate, protein-protein and protein-DNA interactions, etc. Also, reagents that otherwise improve the efficiency of the assay, such as protease inhibitors, nuclease inhibitors, antimicrobial agents, etc. may be used.

The mixture is incubated under conditions whereby the receptor is bound to the ligand and, but for the presence of said candidate pharmacological agent, the labelled protein is sequence-specifically bound to the nucleic acid. The mixture components can be added in any order that provides for the requisite bindings. For example, the nucleic acid conjugate may be added first and prebound to the substrate through ligand-receptor binding before the labelled protein is added. Alternatively, the nucleic acid conjugate and labelled protein can be preincubated and complexed and then added to the substrate for attachment, or the various mixture components and reagents can be added to the substrate simultaneously. Adding the protein and nucleic acid components together may be thermodynamically advantageous in that in some nucleic acid-protein complexes, initial binding may be favored by a soluble, unrestrained nucleic acid molecule.

Incubations may be performed at any temperature which facilitates optimal binding, typically between 4° and 40° C., more commonly between 15° and 40° C. Incubation periods are likewise selected for optimal binding but also minimized to facilitate rapid, high-throughput screening. Typically, protein-nucleic acid and receptor-ligand pairs are coincubated between 0.1 and 10 hours, preferably less than 5 hours, more preferably less than 2 hours each; of course, the incubations may and preferably do run simultaneously.

After receptor-ligand and protein-nucleic acid binding have occurred, a fraction comprising labelled protein which is not sequence-specifically bound is separated from the solid substrate. This step may be accomplished in a variety of ways including removing a bead or dipstick from a reservoir, emptying or diluting reservoir such as a microtiter plate well, rinsing a bead, particle, chromatographic column or filter with a wash solution or solvent. Typically, the separation step will include an extended rinse or wash or a plurality of rinses or washes. For example, where the solid substrate is a microtiter plate, the wells may be washed several times with a washing solution, which typically includes those components of the incubation mixture that do not participate in specific binding such as salts, buffer, detergent, nonspecific protein, etc.

After separating the unbound fraction from the solid substrate, the presence of bound nucleic acid-protein complex is detected via the labeled protein. A variety of methods may be used to detect the label depending on the nature of the label and other assay components. For example, the label may be detected bound to the solid substrate or a portion of the bound complex containing the label may be separated from the solid substrate, and thereafter the label detected. Labels may be directly detected through optical or electron density, radiative emissions, nonradiative energy transfers, etc. or indirectly detected with antibody conjugates, etc. For example, in the case of radioactive labels, emissions may be detected directly, e.g. with particle counters or indirectly, e.g. with scintillation cocktails and counters.

Candidate agents shown to modulate transcription complex formation provide valuable reagents to the pharmaceutical and agricultural industries for cellular, plant, field crop, animal and human trials.

The methods are particularly suited to automated high throughput drug screening. In a preferred embodiment, the individual sample incubation volumes are less than about 500 ul, preferably less than about 250 ul, more preferably less than about 100 ul. Such small sample volumes minimize the use of often scarce candidate agent, expensive transcription complex components, and hazardous radioactive waste. Furthermore, the methods provide for automation, especially computerized automation. Accordingly, the method steps are preferably performed by a computer-controlled electromechanical robot. While individual steps may be separately automated, a preferred embodiment provides a single computer-controlled multifunction robot with a single arm axially rotating to and from a plurality of work stations performing the mixture forming, incubating and separating steps. The computer is loaded with software which provides the instructions which direct the arm and work station operations and provides input (e.g. keyboard and/or mouse) and display (e.g. monitor) means for operator interfacing.

In a particular embodiment, the robotic station comprises a robotic arm 1 with axially-positioned work stations including a working source plate station 2, a working pipette tip station 3, a working assay plate station 4, a liquid dispensing station 5, a wash station 6, an eight channel pipettor station 7, a grip hand station 8, a shaker station 9, a cooling station 10 and a pipet tip storage station 11. The arm retrieves and transfers a microtiler plate to a liquid dispensing station where measured aliquots of each an incubation buffer and a solution comprising one or more candidate agents are deposited into each designated well. The arm then retrieves and transfers to and deposits in designated wells a measured aliquot of a solution comprising a labeled transcription factor protein. After a first incubation period, the liquid dispensing station deposits in each designated well a measured aliquot of a biotinylated nucleic acid solution. The first and/or following second incubation may optionally occur after the arm transfers the plate to a shaker station. After a second incubation period, the arm transfers the microtiter plate to a wash station where the unbound contents of each well is aspirated and then the well repeatedly filled with a wash buffer and aspirated. Where the bound label is radioactive phosphorous, the arm retrieves and transfers the plate to the liquid dispensing station where a measured aliquot of a scintillation cocktail is deposited in each designated well. Thereafter, the mount of label retained in each designated well is quantified.

In more preferred embodiments, the liquid dispensing station and arm are capable of depositing aliquots in at least eight wells simultaneously and the wash station is capable of filling and aspirating ninety-six wells simultaneously. Preferred robots are capable of processing at least 640 and preferably at least about 1,280 candidate agents every 24 hours, e.g. in microtiter plates.

The following examples are offered by way of illustration and not by way of limitation.

EXAMPLES

GENERIC PROTOCOL FOR TRANSCRIPTION FACTOR-DNA BINDING ASSAY

1. Reagents:
Neutralite Avidin: 20% µg/ml in PBS.
Blocking buffer: 5% BSA, 0.5% Tween 20 in PBS; 1 hr, RT.
Assay Buffer: 100 mM KCl, 20 mM HEPES pH 7.6, 0.25 mM EDTA, 1% glycerol, 0.5% NP-40, 50 mM BME, 1 mg/ml BSA, cocktail of protease inhibitors.
$^{33}$P Full-Length Transcription Factor 10× stock: 1–5×10$^{-8}$ "cold" protein comprising unlabeled protein comprising transcription factor portion supplemented with 100,000–500,000 cpm of labeled protein (Beckman counter). Placed in the 4° C. microfridge during screening.
Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml of PBS.
Oligonucleotide stock: (specific biotinylated). Biotinylated oligo at 1–100 pmole/µl, including transcription factor binding site: (BIOTIN)-oligo: e.g. derived from Table 1. anti-sense: derived as reverse complement of target oligo above.

2. Preparation of assay plates:
Coat with 100 µl of stock N-Avidin per well overnight at 4° C.
Wash 2× with 200 µl PBS.
Block with 150 µl of blocking buffer.
Wash 2× with 200 µl PBS.

3. Assay:
Add 40 µl assay buffer/well.
Add 10 µl compound or extract.
Add 10 µl $^{33}$P-labelled protein (10,000–50,000 cpm/well; 10$^{-10}$–10$^{-8}$M final concentration).
Shake at RT for 15 min.
Incubate additional 45 min. at 25 C.
Add 40 µl oligo mixture (1.0 pmoles/40 ul in assay buffer)
Incubate 1 hr at 25 C.
Stop the reaction by washing 4× with 200 µl PBS.
Add 150 µl scintillation cocktail.
Count in Topcount.

PROTOCOL FOR EPSTEIN BARR VIRUS EBNA-1 BINDING ASSAY

1. Reagents:
Neutralite Avidin: 20 µg/ml in PBS.
Blocking buffer: 5% BSA, 0.5% Tween 20 in PBS; 1 hr, RT.
Assay Buffer: 100 mM KCl, 20 mM HEPES pH 7.6, 0.25 mM EDTA, 1% glycerol, 0.5% NP-40, 50 mM BME, 1 mg/ml BSA, cocktail of protease inhibitors.
$^{33}$P EBNA 10× stock: 3×10$^{-8}$ "cold" EBNA (M.W. ~40,000 for dimer) supplemented with 200,000–250,000 cpm of labeled EBNA-1 (Beckman counter). This is to be placed in the 4° C. microfridge during screening.
Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml of PBS.

Oligonucleotide stock: (specific biotinylated). Biotinylated oligo at 17 pmole/µl, EBNA site TO889/832: (BIOTIND-GGA TCT GGT TAG CAT ATG CTA ACC AGG ATC (SEQ ID NO: 60) anti-sense-GAT CIT GGT TAG CAT ATG CTA ACC AGA TCC (SEQ ID NO: 65)

2. Preparation of assay plates:

Coat with 100 µl of stock N-Avidin per well overnight at 4° C.
Wash 2× with 200 µl PBS.
Block with 150 µl of blocking buffer.
Wash 2× with 200 µl PBS.

3. Assay:

Add 40 µl assay buffer/well.
Add 10 µl compound or extract.
Add 10 µl $^{33}$P-EBNA-1 (20,000–25,000 cpm/0.3 pmoles/well=3×10$^{-9}$M final concentration).
Shake at RT for 15 min.
Incubate additional 45 min. at RT.
Add 40 µl oligo mixture (1.0 pmoles/40 ul in assay buffer).
Incubate 1 hr at RT.
Stop the reaction by washing 4× with 200 µl PBS.
Add 150 µl scintillation cocktail.
Count in Topcount.

PROTOCOL FOR EPSTEIN BARR VIRUS BZLF-1 BINDING ASSAY

1. Reagents:

Neutralite Avidin: 20 µg/ml in PBS.
Blocking buffer: 5% BSA, 0.5% Tween 20 in PBS; 1 hr, RT.
Assay Buffer: 100 mM KCl, 20 mM HEPES pH 7.6, 0.25 mM EDTA, 1% glycerol, 0.5% NP-40, 50 mM BME, 1 mg/ml BSA, cocktail of protease inhibitors.
$^{33}$P Full-Length BZLF 10× stock: 1×10$^{-8}$ "cold" BZLF supplemented with 180,000–220,000 cpm of labeled BZLF (Beckman counter), resulting in an approx. specific activity of 180,000–220,000 cpm/1 pmole (M.W. ~54,000 for dimer). The protein stock solution contains 70% Et-OH, 30% assay buffer without BSA, and 50 mM BME (final concentration). The protein is to be placed in the 4° C. microfridge during screening.
Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml of PBS.
Oligonucleotide stock: (specific biotinylated). Biotinylated oligo at 22 pmole/µl, BZLF site TO855/854: sense-(BIOTIN) TTAT CTA CAT TAG CAA TGC CTT AGC AAT GTG CAT A (SEQ ID NO: 66) anti-sense-TAT GCA CAT TGC TAA GGC ATE GCT AAT GTA GAT A (SEQ ID NO: 67)

2. Preparation of assay plates:

Coat with 100 µl of stock N-Avidin per well overnight at 4° C.
Wash 2× with 200 µl PBS.
Block with 150 µl of blocking buffer.
Wash 2× with 200 µl PBS.

3. Assay:

Add 40 µl assay buffer/well.
Add 10 µl compound or extract.
Add 10 µl $^{33}$P-BZLF (18,000–22,000 cpm/0.1 pmoles/well= 1×10$^{-9}$M final concentration).
Shake at RT for 15 min.
Incubate additional 45 min. at RT.
Add 40 µl oligo mixture (1.0 pmoles/40 ul in assay buffer)
Incubate 1 hr at RT.

Stop the reaction by washing 4× with 200 µl PBS.
Add 150 µl scintillation cocktail.
Count in Topcount.

PROTOCOL FOR HUMAN PAPILOMA VIRUS 6 E2 BINDING ASSAY

1. Reagents:

Neutralite Avidin: 20 µl /ml in PBS.
Blocking buffer: 5% BSA, 0.5% Tween 20 in PBS; 1 hr, 25 C.
Assay Buffer: 100 mM KCl, 20 mM HEPES pH 7.6, 0.25 mM EDTA, 1% glycerol, 0.5% NP-40, 50 mM BME, 1 mg/ml BSA, cocktail of protease inhibitors.
$^{33}$P Full-Length E2 10× stock: 1×10$^{-8}$ "cold" E2 supplemented with 200,000–300,000 cpm of labeled E2, resulting in an approx. specific activity of 200,000–300,000 cpm/1 pmole (M.W. ~100 kD for dimer). Place in microfridge set at 4° C.
Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml of PBS.
Oligonucleotide stock: (specific biotinylated and sheared salmon sperm (sss)-DNA). Biotinylated oligo at 25 pmoles/ml, HPV-E2 1 site TO922/923: (BIOTIN)-CCA GAG TGA CCG AAA ACG GTG TGA GAG C (SEQ ID NO: 68) anti-sense- GGT CTC ACA CCG TIT TCG GTC ACT CTG G (SEQ ID NO: 69) and sss-DNA at 25 µg/ml in assay buffer.

2. Preparation of assay plates:

Coat with 100 µl of stock N-Avidin per well overnight at 4° C.
Wash 2× with 200 µl PBS.
Block with 150 µl of blocking buffer.
Wash 2× with 200 µl PBS.

3. Assay:

Add 40 µl assay buffer/well.
Add 10 µl compound or extract.
Add 10 µl $^{33}$P-E2 (20,000–30,000 cpm/0.1 pmoles/well=1×10$^{-9}$M final concentration).
Shake at 25 C for 15 min.
Incubate additional 45 min. at 25 C.
Add 40 µl oligo mixture (1 pmole of biotinylated specific oligo and 1 µg of sss-DNA)
Incubate 1 hr at 25 C.
Stop the reaction by washing 4× with 200 µl PBS.
Add 150 µl scintillation cocktail.
Count in Topcount.

4. Controls:

a. Non-specific binding (no oligo added)
b. Specific soluble oligo at 80% inhibition

PROTOCOL FOR Nf-kB BINDING ASSAY (p65/p50)

1. Reagents:

Neutralite Avidin: 50 µg/ml in PBS.
Blocking buffer: 5% BSA, 0.5% Tween 20 in PBS; 1 hr, RT.
Assay Buffer: 100 mM KCl, 20 mM HEPES pH 7.9, 0.5 mM EDTA, 1% glycerol, 0.5% NP-40, 1 mg/ml BSA, 50 mM BME, cocktail of protease inhibitors.
$^{33}$Pp65/p65/p50 10× stock: 1×10$^{-8}$ "cold" p65/p50 (5×10$^{-9}$M p65+5×10$^{-9}$ M p50 supplemented with 200,000–300,000 cpm of labeled p65, resulting in an approx. specific activity of 200,000–300,000 cpm/1 pmole. Heterodimer formation is promoted by incubating the mixture for 1 hr at 37° C prior to use.

Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml of PBS.

Biotinylated oligo: 40× stock at 1 pmoles/1 µl in assay buffer. ELAM 2 site END-126/127: (BIOTIN)-CAA CAG ATT GGG GAT ITC CTC GGT TCC ATT GGG GAT TTC CTC CAG C (SEQ ID NO: 70) anti-sense-GC TGA GAG GAA ATC CCC AAT GGA ACC GAG GAA ATC CCC AAT CTG TTG (SEQ ID NO: 71)

2. Preparation of assay plates:

Coat with 100 µl of stock N-Avidin per well overnight at 4° C.
Wash 2× with 200 µl PBS.
Block with 150 µl of blocking buffer.
Wash 2× with 200 µl PBS.

3. Assay:

Add 40 µl assay buffer/well.
Add 10 µl compound or extract.
Add 10 µl $^{33}$P-p65/p50 (20,000–30,000 cpm/0.1 pmoles/well=1×10$^{-9}$M final concentration).
Shake at RT for 15 min.
Incubate additional 45 min. at RT.
Add 40 µl biotinylated oligo (1.0 pmole/40 µl /well) in assay buffer.
Incubate 1 hr at RT.
Stop the reaction by washing 4× with 200 µl PBS.
Add 150 µl scintillation cocktail.
Count in Topcount.

PROTOCOL FOR Nf-kB BINDING ASSAY
(p65/p65)

1. Reagents:

Neutralite Avidin: 20 µg/ml in PBS.
Blocking buffer: 5% BSA, 0.5% Tween 20 in PBS; 1 hr, RT.
Assay Buffer: 100 mM KCl, 20 mM HEPES pH 7.9, 0.5 mM EDTA, 1% glycerol, 0.5% NP-40, 1 mg/ml BSA, 50 mM BME, cocktail of protease inhibitors.
$^{33}$Pp65/p65 10× stock: 1×10$^{-8}$ "cold" p65 supplemented with 200,000–300,000 cpm of labeled p65, resulting in an approx. specific activity of 200,000–300,000 cpm/ 1 pmole.
Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml of PBS.
Biotinylated oligo: 40× stock at 1 pmoles/1 µl in assay buffer. ELAM 2 site END-126/127: (BIOTIN) -CAA CAG ATE GGG GAT TTC CTC GGT TCC ATE GGG GAT TEC CTC CAG C (SEQ ID NO: 70) anti-sense-GC TGA GAG GAA ATC CCC AAT GGA ACC GAG GAA ATC CCC AAT CTG TTG (SEQ ID NO: 72)

2. Preparation of assay plates:

Coat with 100 µl of stock N-Avidin per well overnight at 4° C.
Wash 2× with 200 µl PBS.
Block with 150 µl of blocking buffer.
Wash 2× with 200 µl PBS.

3. Assay:

Add 40 µl assay buffer/well.
Add 10 µl compound or extract.
Add 10 µl $^{33}$P-p65 (20,000–30,000 cpm/0.1 pmoles/well= 1×10$^{-9}$M final concentration).
Shake at RT for 15 min.
Incubate additional 45 min. at RT.
Add 40 µl biotinylated oligo (1.0 pmole/50 µl /well) in assay buffer.
Incubate 1 hr at RT.
Stop the reaction by washing 4× with 200 µl PBS.
Add 150 µl scintillation cocktail.
Count in Topcount.

PROTOCOL FOR HERPES SIMPLEX VIRUS VP-16 BINDING ASSAY

1. Reagents:

Neutralite Avidin: 20 µg/ml in PBS.
Blocking buffer: 5% BSA, 0.5% Tween 20 in PBS; 1 hr, 25C.
Assay Buffer: 100 mM KCl, 20 mM HEPES pH 7.6, 0.25 mM EDTA, 1% glycerol, 0.5% NP-40, 50 mM BME, 1 mg/ml BSA, cocktail of protease inhibitors.
$^{33}$P Truncated VP-16/HCF/OCT-1 10× stock mix: 1×10$^{-8}$ "cold" VP-16 supplemented with 250,000–300,000 cpm of labeled VP-16, resulting in an approx. specific activity of 250,000–300,000 cpm/1 pmole (M.W. ~18 kD), 50 µl HCF, and 500 ng of OCT-1 per ml of the stock mix. Place in microfridge set at 4° C.
Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml of PBS.
Oligonucleotide stock: (specific biotinylated and sss-DNA). Biotinylated oligo at 25 pmole/ml, HSV-VP-16 TO876/877: sen se-Biotin T-GAT AGT CAG GAC TGA ATG CCG TGC ATG CTA ATG ATA TTC TIT GCT TGA TC (SEQ ID NO: 73); anti-sense- GAT CAA GCA AAG AAT ATC ATT AGC ATG CAC GGC ATT CAG TCC TGA CTA TC (SEQ ID NO: 74) and sss-DNA at 2.5 µg/ml in assay buffer.

2. Preparation of assay plates:

Coat with 120 µl of stock N-Avidin per well overnight at 4° C.
Wash 2× with 200 µl PBS.
Block with 150 µl of blocking buffer.
Wash 2× with 200 µl PBS.

3. Assay:

Add 40 µl assay buffer/well.
Add 10 µl compound or extract.
Add 10 µl $^{33}$P-VP-16, HCF, OCT-1 stock (25,000–30,000 cpm/0.1 pmoles/well=1×10$^{-9}$M final concentration, 0.5 µl HCF, and 5 ng OCT-1)
Shake at 25 C for 15 min.
Incubate additional 45 min. at 25 C.
Add 40 µl oligo mixture (1 pmole of biotinylated specific oligo and 100 ng of ss-DNA)—Incubate 1 hr at 25 C.
Stop the reaction by washing 4× with 200 µl PBS.
Add 150 µl scintillation cocktail.
Count in Topcount.

4. Controls for all assays (located on each plate):
a. Non-specific binding (no oligo added)
b. Specific soluble oligo at 80% inhibition.

PROTOCOL FOR HIV TAT BINDING ASSAY

1. Reagents:

Neutralite Avidin: 20 µg/ml in PBS.
Blocking buffer: 5% BSA, 0.5% Tween 20 in PBS; 1 hr, RT.
Assay Buffer: 100 mM KCl, 20 mM HEPES pH 7.9, 0.5 mM EDTA, 1% glycerol, 0.5% NP-40, 1 mg/ml BSA, 50 mM BME, cocktail of protease inhibitors.

$^{33}$PTAT10× stock: 1×10$^{-8}$ "cold" p65 supplemented with 200,000–300,000 cpm of labeled TAT, resulting in an approx. specific activity of 200,000–300,000 cpm/1 pmole.

Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml of PBS.

Biotinylated oligo: 40× stock at 1 pmoles/1 μl in assay buffer. TAR RNA site: (BIOTIN) -GGG TCT CTC TGG TTA GAC CAG ATC TGA GCC TGG GAG CTC TCT GGC TAA CTA GGG AAC CCA (SEQ ID NO: 75)

2. Preparation of assay plates:

Coat with 100 μl of stock N-Avidin per well overnight at 4° C.
Wash 2× with 200 μl PBS.
Block with 150 μl of blocking buffer.
Wash 2× with 200 μl PBS.

3. Assay:

Add 40 μl assay buffer/well.
Add 10 μl compound or extract.
Add 10 μl $^{33}$P-pTAT (20,000–30,000 cpm/0.1 pmoles/well= 1×10$^{-9}$M final concentration).
Shake at RT for 15 min.
Incubate additional 45 min. at RT.
Add 40 μl biotinylated oligo (1.0 pmole/50 μl /well) in assay buffer.
Incubate 1 hr at RT.
Stop the reaction by washing 4× with 200 μl PBS.
Add 150 μl scintillation cocktail.
Count in Topcount.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the an in light of the teachings of this invention that certain changes and modifications may be made thereto without departing from the spirit or scope of the appended claims.

---

What is claimed is:

1. A method of screening for a compound which inhibits the binding of a transcription factor to a nucleic acid, said method comprising the steps of:

forming a mixture by combining a labeled protein comprising a portion of a transcription factor and a label, a nucleic acid conjugate, said compound and a receptor immobilized on a solid substrate, wherein said nucleic acid conjugate comprises a nucleotide sequence and a ligand which specifically binds said receptor;

incubating said mixture under conditions whereby said receptor is bound to said ligand, and wherein in the absence of said compound said labeled protein is sequence-specifically bound to said nucleic acid conjugate;

separating from said solid substrate a fraction of said mixture, which fraction comprises said labeled protein if said labeled protein is not sequence-specifically bound to said nucleic acid conjugate; and detecting the presence or absence of said label on said solid substrate, wherein the absence of said label on said solid substrate indicates said compound inhibits the binding of said transcription factor to said nucleic acid.

2. A method according to claim 1, wherein said labeled protein sequence-specifically binds said nucleic acid conjugate with a binding affinity of at least $10^6$ M$^{-1}$.

3. A method according to claim 1, wherein said mixture further comprises a portion of an auxiliary protein which enhances binding of said labeled protein to said nucleic acid conjugate.

4. A method according to claim 1, wherein said transcription factor is a viral transcription factor.

5. A method according to claim 1, wherein said transcription factor is a bacterial transcription factor.

6. A method according to claim 1, wherein said transcription factor is a plant transcription factor.

7. A method recording to claim 1, wherein transcription factor is a fungal transcription factor.

8. A method according to claim 1, wherein said transcription factor is a monocotyledonous or dicotyledonous plant transcription factor.

9. A method according to claim 1, wherein said receptor is avidin and said ligand is biotin.

10. A method according to claim 1, wherein said label is a radioactive phosphorous atom.

11. A method according to claim 1, wherein said forming step and said separating step are performed at least in part by a computer controlled electromechanical robot.

12. A method according to claim 11, wherein said robot comprises an axial rotatable arm and said solid substrate is a microliter plate.

13. A kit for screening for a compound which inhibits the binding of a transcription factor to a nucleic acid, said kit comprising:

a solid substrate, a labeled protein comprising a portion of a transcription factor and a label, said compound, a receptor immobilized on said solid substrate, and a nucleic acid conjugate comprising a nucleotide sequence and a ligand which specifically binds said receptor.

14. A kit according to claim 13, further comprising a computer-controllable electromagnetic robot with an axial rotatable arm and wherein said solid substrate is a microtiter plate.

* * * * *

SEQUENCE LISTING ( 1 ) GENERAL INFORMATION:

( i i i ) NUMBER OF SEQUENCES: 75

( 2 ) INFORMATION FOR SEQ ID NO:1:

( i ) SEQUENCE CHARACTERISTICS:
( A ) LENGTH: 14 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:1:

TTTCATATTA CTCT 14

( 2 ) INFORMATION FOR SEQ ID NO:2:

( i ) SEQUENCE CHARACTERISTICS:
( A ) LENGTH: 12 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:2:

TGCGTGAGAA GA 12

( 2 ) INFORMATION FOR SEQ ID NO:3:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:3:

YCAGCTGYGG 10

( 2 ) INFORMATION FOR SEQ ID NO:4:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

AGAACANNNT GTTCT                                                                 15

( 2 ) INFORMATION FOR SEQ ID NO:5:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

TGANCCCTTG ACCCCT                                                                16

( 2 ) INFORMATION FOR SEQ ID NO:6:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

GGGGGGGGGG GGGGGG                                                                16

( 2 ) INFORMATION FOR SEQ ID NO:7:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

GACGCANYGR WNNNMG                                                                16

( 2 ) INFORMATION FOR SEQ ID NO:8:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

ACACCCAAAT ATGGCGAC                                                              18

( 2 ) INFORMATION FOR SEQ ID NO:9:

( i ) SEQUENCE CHARACTERISTICS:
        ( A ) LENGTH: 13 base pairs ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

GTGTCAAAGG TCA 13

( 2 ) INFORMATION FOR SEQ ID NO:10:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

YNNNNNNRRC CAATCANYK 19

( 2 ) INFORMATION FOR SEQ ID NO:11:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

YAGYNNNRRC CAATCNNNR 19

( 2 ) INFORMATION FOR SEQ ID NO:12:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

CCGCCCCCGC 10

( 2 ) INFORMATION FOR SEQ ID NO:13:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

AGGTCANNNT GACCT 15

( 2 ) INFORMATION FOR SEQ ID NO:14:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

GTGTCAAAGG TCA                                                                                                13

( 2 ) INFORMATION FOR SEQ ID NO:15:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

CAGCCCCGC GCAGC                                                                                               15

( 2 ) INFORMATION FOR SEQ ID NO:16:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

AGAACANNNT GTTCT                                                                                              15

( 2 ) INFORMATION FOR SEQ ID NO:17:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

GCACCAATCA CAGCGCGC                                                                                           18

( 2 ) INFORMATION FOR SEQ ID NO:18:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:

TCAGGTCACA GTGACCTGA                                                                                          19

( 2 ) INFORMATION FOR SEQ ID NO:19:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:19:

TGGGGATTCC CCA                                                                                                13

( 2 ) INFORMATION FOR SEQ ID NO:20:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:20:

GTTAATNATT AAC     13

( 2 ) INFORMATION FOR SEQ ID NO:21:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:21:

TATTGAYTTW G     11

( 2 ) INFORMATION FOR SEQ ID NO:22:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:22:

KGCWARGKYC AY     12

( 2 ) INFORMATION FOR SEQ ID NO:23:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:23:

NGAANNGAAN NGAAN     15

( 2 ) INFORMATION FOR SEQ ID NO:24:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:24:

GCCATCTGCT     10

( 2 ) INFORMATION FOR SEQ ID NO:25:

( i ) SEQUENCE CHARACTERISTICS:
        ( A ) LENGTH: 16 base pairs ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:25:

CGGGAAATGG AAACTG 16

( 2 ) INFORMATION FOR SEQ ID NO:26:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:26:

CTTTCAGTTT 10

( 2 ) INFORMATION FOR SEQ ID NO:27:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:27:

CTTTCTCTTT 10

( 2 ) INFORMATION FOR SEQ ID NO:28:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:28:

GCTTCAGTTT 10

( 2 ) INFORMATION FOR SEQ ID NO:29:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:29:

TGGGGATTCC CCA 13

( 2 ) INFORMATION FOR SEQ ID NO:30:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:30:

GCCTGCAGGC                                                                                          10

( 2 ) INFORMATION FOR SEQ ID NO:31:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:31:

GTTAATNATT AAC                                                                                      13

( 2 ) INFORMATION FOR SEQ ID NO:32:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:32:

GCGCCCTTTG GACCT                                                                                    15

( 2 ) INFORMATION FOR SEQ ID NO:33:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:33:

YTAAAAATAA YYY                                                                                      13

( 2 ) INFORMATION FOR SEQ ID NO:34:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:34:

TGGGGATTCC CCA                                                                                      13

( 2 ) INFORMATION FOR SEQ ID NO:35:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:35:

YTAWAAATAR                                                                                          10

( 2 ) INFORMATION FOR SEQ ID NO:36:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:36:

AGAACANNNT GTTCT     15

( 2 ) INFORMATION FOR SEQ ID NO:37:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..14
        ( D ) OTHER INFORMATION: /note="Where this sequence can
            contain 5 or 6 N nucleotides"

( x i ) SEQUENCE DESCRIPTION: SEQ ID NO:37:

YGGMNNNNNG CCAA     14

( 2 ) INFORMATION FOR SEQ ID NO:38:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:38:

GGAGGAAAAA CTGTTTCAT     19

( 2 ) INFORMATION FOR SEQ ID NO:39:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:39:

GRGRTTKCAY     10

( 2 ) INFORMATION FOR SEQ ID NO:40:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:40:

GGGAMTNYCC     10

( 2 ) INFORMATION FOR SEQ ID NO:41:

( i ) SEQUENCE CHARACTERISTICS:
       ( A ) LENGTH: 12 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:41:

AGGTCATGAC CT                                                                                                  12

( 2 ) INFORMATION FOR SEQ ID NO:42:

( i ) SEQUENCE CHARACTERISTICS:
       ( A ) LENGTH: 23 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:42:

CACCGTTCCG CTCTAGATAT CTC                                                                                      23

( 2 ) INFORMATION FOR SEQ ID NO:43:

( i ) SEQUENCE CHARACTERISTICS:
       ( A ) LENGTH: 14 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:43:

AGAAAGGGAA AGGA                                                                                                14

( 2 ) INFORMATION FOR SEQ ID NO:44:

( i ) SEQUENCE CHARACTERISTICS:
       ( A ) LENGTH: 15 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:44:

AGAACANNNT GTTCT                                                                                               15

( 2 ) INFORMATION FOR SEQ ID NO:45:

( i ) SEQUENCE CHARACTERISTICS:
       ( A ) LENGTH: 10 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:45:

AAGTGAAAGT                                                                                                     10

( 2 ) INFORMATION FOR SEQ ID NO:46:

( i ) SEQUENCE CHARACTERISTICS:

( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..18
        ( D ) OTHER INFORMATION: /note="Where N is one or more
            nucleotides."

( x i ) SEQUENCE DESCRIPTION: SEQ ID NO:46:

ATGGGANCTC AGCTGTGC                                                             18

( 2 ) INFORMATION FOR SEQ ID NO:47:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:47:

AGGTCATGAC CT                                                                   12

( 2 ) INFORMATION FOR SEQ ID NO:48:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:48:

CCCCTAGCAA CAGATG                                                               16

( 2 ) INFORMATION FOR SEQ ID NO:49:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:49:

AAGATAAAAC C                                                                    11

( 2 ) INFORMATION FOR SEQ ID NO:50:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:50:

GGATGTCCAT ATTAGGACAT CT                                                        22

( 2 ) INFORMATION FOR SEQ ID NO:51:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:51:

AAGTGTTTGC      10

( 2 ) INFORMATION FOR SEQ ID NO:52:

( i ) SEQUENCE CHARACTERISTICS:
    ( A ) LENGTH: 10 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:52:

AGGAAGTTCC      10

( 2 ) INFORMATION FOR SEQ ID NO:53:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:53:

TCTTCTCACG CAACT      15

( 2 ) INFORMATION FOR SEQ ID NO:54:

( i ) SEQUENCE CHARACTERISTICS:
    ( A ) LENGTH: 16 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:54:

CACCTGNNNN TTTCCC      16

( 2 ) INFORMATION FOR SEQ ID NO:55:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:55:

ATTTTTCTGA TTGGCCAAAG      20

( 2 ) INFORMATION FOR SEQ ID NO:56:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:56:

GGTTAGCATA TGCTAACCA        19

( 2 ) INFORMATION FOR SEQ ID NO:57:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:57:

ACCGAAAACG GTGT        14

( 2 ) INFORMATION FOR SEQ ID NO:58:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:58:

ATGCTAATGA TA        12

( 2 ) INFORMATION FOR SEQ ID NO:59:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:59:

GGGTCTCTCT GGTTAGACCA GATCTGAGCC TGGGAGCTCT CTGGCTAACT AGGGAACCCA        60

( 2 ) INFORMATION FOR SEQ ID NO:60:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:60:

GGATCTGGTT AGCATATGCT AACCAGGATC        30

( 2 ) INFORMATION FOR SEQ ID NO:61:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:61:

GGATCTGGTA CCGAAAACGG TACCAGGATC     30

( 2 ) INFORMATION FOR SEQ ID NO:62:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:62:

GGATCTGGTT AGTTAGCAAT GACCAGGATC     30

( 2 ) INFORMATION FOR SEQ ID NO:63:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:63:

GGATCTGGTT AGGGGATTTC CACCAGGATC     30

( 2 ) INFORMATION FOR SEQ ID NO:64:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:64:

GGATCTGGTT ATGCTAATGA TATCAGGATC     30

( 2 ) INFORMATION FOR SEQ ID NO:65:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:65:

GATCTTGGTT AGCATATGCT AACCAGATCC     30

( 2 ) INFORMATION FOR SEQ ID NO:66:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:66:

TATCTACATT AGCAATGCCT TAGCAATGTG CATA     34

( 2 ) INFORMATION FOR SEQ ID NO:67:

( i ) SEQUENCE CHARACTERISTICS:
 ( A ) LENGTH: 34 base pairs
 ( B ) TYPE: nucleic acid
 ( C ) STRANDEDNESS: single
 ( D ) TOPOLOGY: linear ( i i ) MOLECULE TYPE: cDNA ( x i ) SEQUENCE DESCRIPTION: SEQ ID NO:67:

TATGCACATT GCTAAGGCAT TGCTAATGTA GATA 34

( 2 ) INFORMATION FOR SEQ ID NO:68:

( i ) SEQUENCE CHARACTERISTICS:
  ( A ) LENGTH: 28 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:68:

CCAGAGTGAC CGAAAACGGT GTGAGACC 28

( 2 ) INFORMATION FOR SEQ ID NO:69:

( i ) SEQUENCE CHARACTERISTICS:
  ( A ) LENGTH: 28 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:69:

GGTCTCACAC CGTTTTCGGT CACTCTGG 28

( 2 ) INFORMATION FOR SEQ ID NO:70:

( i ) SEQUENCE CHARACTERISTICS:
  ( A ) LENGTH: 46 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:70:

CAACAGATTG GGGATTTCCT CGGTTCCATT GGGGATTTCC TCCAGC 46

( 2 ) INFORMATION FOR SEQ ID NO:71:

( i ) SEQUENCE CHARACTERISTICS:
  ( A ) LENGTH: 47 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:71:

GCTGAGAGGA AATCCCCAAT GGAACCGAGG AAATCCCCAA TCTGTTG 47

( 2 ) INFORMATION FOR SEQ ID NO:72:

( i ) SEQUENCE CHARACTERISTICS:
  ( A ) LENGTH: 47 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:72:

GCTGAGAGGA AATCCCCAAT GGAACCGAGG AAATCCCCAA TCTGTTG    47

( 2 ) INFORMATION FOR SEQ ID NO:73:

( i ) SEQUENCE CHARACTERISTICS:
 ( A ) LENGTH: 50 base pairs
 ( B ) TYPE: nucleic acid
 ( C ) STRANDEDNESS: single
 ( D ) TOPOLOGY: linear ( i i ) MOLECULE TYPE: cDNA ( x i ) SEQUENCE DESCRIPTION: SEQ ID NO:73:

GATAGTCAGG ACTGAATGCC GTGCATGCTA ATGATATTCT TTGCTTGATC    50

( 2 ) INFORMATION FOR SEQ ID NO:74:

( i ) SEQUENCE CHARACTERISTICS:
 ( A ) LENGTH: 50 base pairs
 ( B ) TYPE: nucleic acid
 ( C ) STRANDEDNESS: single
 ( D ) TOPOLOGY: linear ( i i ) MOLECULE TYPE: cDNA ( x i ) SEQUENCE DESCRIPTION: SEQ ID NO:74:

GATCAAGCAA AGAATATCAT TAGCATGCAC GGCATTCAGT CCTGACTATC    50

( 2 ) INFORMATION FOR SEQ ID NO:75:

( i ) SEQUENCE CHARACTERISTICS:
 ( A ) LENGTH: 60 base pairs
 ( B ) TYPE: nucleic acid
 ( C ) STRANDEDNESS: single
 ( D ) TOPOLOGY: linear ( i i ) MOLECULE TYPE: cDNA ( x i ) SEQUENCE DESCRIPTION: SEQ ID NO:75:

GGGTCTCTCT GGTTAGACCA GATCTGAGCC TGGGAGCTCT CTGGCTAACT AGGGAACCCA    60